US012709729B2

(12) United States Patent
Kim et al.

(10) Patent No.: US 12,709,729 B2
(45) Date of Patent: Aug. 18, 2026

(54) DEVICE WITH CELL ANALYSIS

(71) Applicant: Samsung Electronics Co., Ltd., Suwon-si (KR)

(72) Inventors: Jonghan Kim, Suwon-si (KR); Chisung Bae, Suwon-si (KR); Mikyung Kim, Suwon-si (KR); Takhyung Lee, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 570 days.

(21) Appl. No.: 18/366,818

(22) Filed: Aug. 8, 2023

(65) Prior Publication Data

US 2024/0174969 A1 May 30, 2024

(30) Foreign Application Priority Data

Nov. 29, 2022 (KR) ........................ 10-2022-0163063

(51) Int. Cl.
*C12M 1/34* (2006.01)
*G01N 33/50* (2006.01)

(52) U.S. Cl.
CPC ......... *C12M 41/46* (2013.01); *G01N 33/5005* (2013.01)

(58) Field of Classification Search
None
See application file for complete search history.

(56) References Cited

U.S. PATENT DOCUMENTS

2019/0391127 A1* 12/2019 Braeken ................. C12M 41/46
2021/0371846 A1* 12/2021 Ham ...................... A61B 5/053
2022/0263510 A1* 8/2022 Faldu ...................... A61B 5/24

FOREIGN PATENT DOCUMENTS

CN 114252483 A 3/2022
KR 10-1616294 B1 1/2022

OTHER PUBLICATIONS

Ham, Donhee, et al. "Neuromorphic electronics based on copying and pasting the brain." *Nature Electronics* 4.9 (Sep. 2021): pp. 635-644.

* cited by examiner

*Primary Examiner* — Ann Montgomery
(74) *Attorney, Agent, or Firm* — NSIP Law

(57) ABSTRACT

A computing device is provided. The computing device includes an electrode layer comprising a plurality of micro-electrode arrays (MEAs), each MEA being configured with electrodes for stimulation and sensing of biological cells; an interposer layer comprising an interposer for a wiring connection between the plurality of MEAs and a substrate of the computing device; a circuit layer comprising a plurality of circuit chips configured to stimulate the cells and store excitement of the cells in response to the stimulation by corresponding electrodes; and a controller configured to control whether or how to connect the plurality of circuit chips to the plurality of MEAs.

20 Claims, 5 Drawing Sheets

DEVICE WITH CELL ANALYSIS

CROSS-REFERENCE TO RELATED APPLICATIONS

This application claims the benefit under 35 USC § 119(a) of Korean Patent Application No. 10-2022-0163063, filed on Nov. 29, 2022, in the Korean Intellectual Property Office, the entire disclosure of which is incorporated herein by reference for all purposes.

BACKGROUND

1. Field

The following description relates to a device with cell analysis.

2. Description of Related Art

Biometric signals may be analyzed using various methods. For example, brain waves are typically analyzed using signals of neurons measured by a plurality of electrodes. In addition, a signal transmission method in the brain may be interpreted by sending a predetermined amount of current to brain nerve cells and observing intracellular signals. For large-scale biological neural network, for example, it may be analyzed using multi-electrode array (MEA) electrodes.

SUMMARY

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In one general aspect, a computing device includes an electrode layer comprising a plurality of microelectrode arrays (MEAs), each MEA being configured with electrodes for stimulation and sensing of biological cells; an interposer layer comprising an interposer for a wiring connection between the plurality of MEAs and a substrate of the computing device; a circuit layer comprising a plurality of circuit chips configured to stimulate the cells and store excitement of the cells in response to the stimulation by corresponding electrodes; and a controller configured to control whether or how to connect the plurality of circuit chips to the plurality of MEAs.

The interposer layer may include the electrode layer with the interposer layer and the circuit layer being connected to each other by flip-chip bonding.

The electrode layer may be formed on one side of the substrate on which the interposer layer is formed, and the circuit layer may be formed on the one side of the substrate or on an opposing side of the substrate.

The controller may be configured to determine whether or how to connect the plurality of circuit chips to the plurality of respective MEAs, based on at least one of a number of the electrodes used for the stimulation and the sensing of the cells, or based on positions of the electrodes used for the stimulation.

The controller may be configured to select a number of circuit chips used among the plurality of circuit chips and determine positions of the selected circuit chips, based on at least one of a number of the electrodes used for the stimulation and the sensing of the cells, or positions of the electrodes used for the stimulation.

The controller, based on whether the plurality of circuit chips are activated, may be configured to selectively use electrodes corresponding to an activated circuit chip among the plurality of MEAs.

The electrodes corresponding to the activated circuit chip may include at least one of electrodes positioned adjacent to each other in one MEA corresponding to the activated circuit chip; electrodes spaced apart from each other in one MEA corresponding to the activated circuit chip; and electrodes spaced apart from each other in a plurality of MEAs corresponding to the activated circuit chip.

In the computing device, a number of the electrodes used for stimulation and an arrangement of the electrodes for the stimulation may be determined based on bonding positions of corresponding circuit chips and a number of the corresponding circuit chips.

The plurality of MEAs may be packaged on the substrate by centrally integrated electrode pads.

In the computing device, sizes of at least some of the plurality of MEAs may be same or different from each other.

In the computing device, respective types and sizes of at least some of the plurality of circuit chips may be same or different from each other.

The electrode layer and the interposer layer may be connected by flip-chip bonding by at least one of a micro bump or a through silicon via (TSV) including a fine line width.

The plurality of circuit chips and the interposer layer may be connected to each other by at least one of a micro bump, a redistributed layer (RDL), or a through silicon via (TSV) including a fine line width.

In the computing device, an electrode pad for the plurality of MEAs may be disposed on the interposer layer or an upper portion of the substrate, and a bonding pad for the plurality of circuit chips may be disposed on the upper portion of the substrate or a lower portion of the substrate.

In the computing device, a total number of MEAs may be same as a total number of circuit chips.

The plurality of circuit chips and the plurality of MEAs may be matched one-to-one or one-to-many.

The interposer layer may include a redistributed layer (RDL), and the plurality of circuit chips and the electrodes of the plurality of MEAs may be connected to each other through the RDL.

The substrate may include one of a printed circuit board (PCB) and a silicon substrate.

The plurality of MEAs may be packaged to be waterproof.

The computing device may further include a cell culture vessel comprising a cell culture medium that cultures the cells, wherein the electrode layer and the cell culture vessel may be disposed adjacent to each other.

Other features and aspects will be apparent from the following detailed description, the drawings, and the claims.

Figure 1:
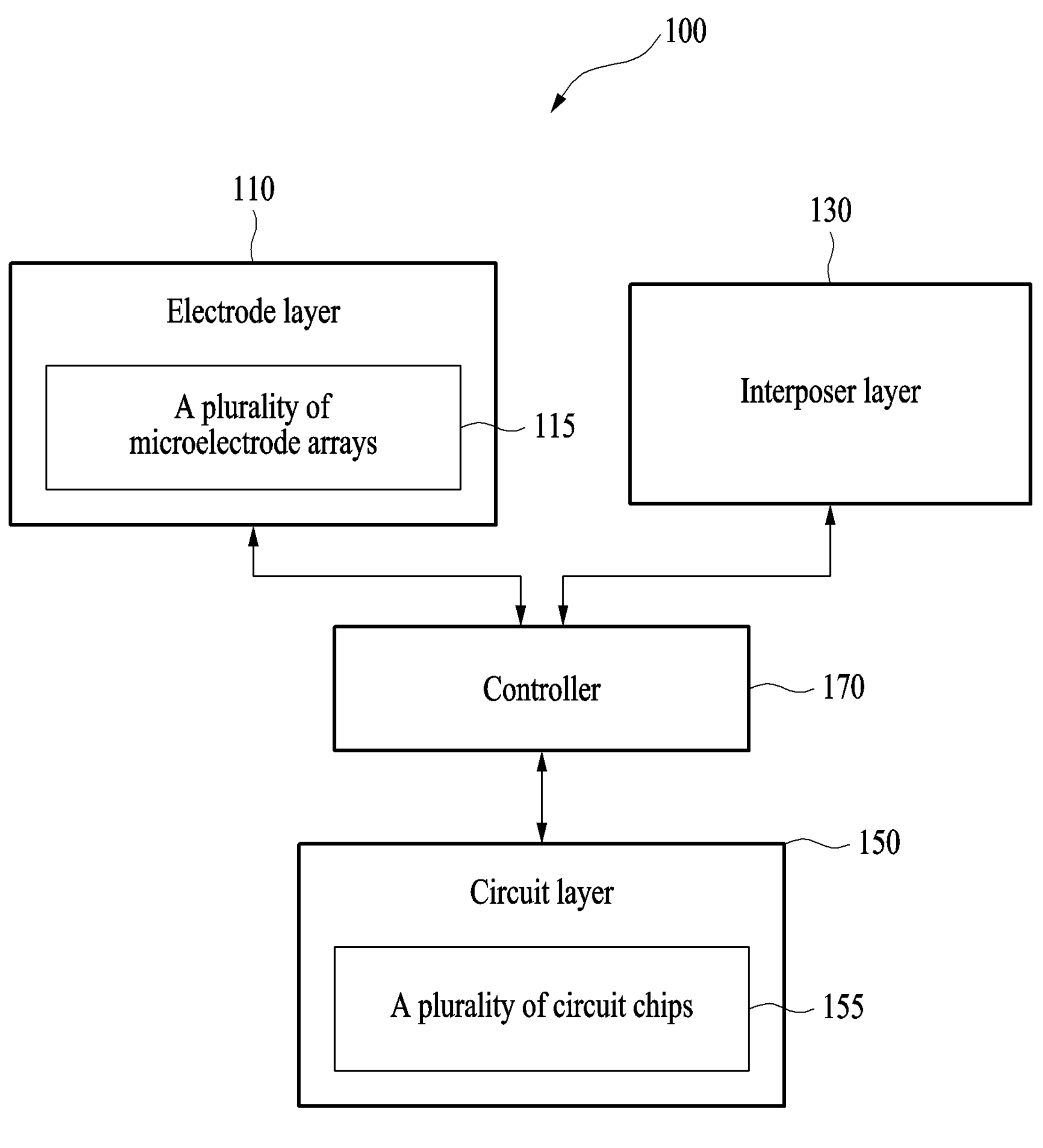
FIG. 1 illustrates an example computing device with cell analysis according to one or more embodiments.

Throughout the drawings and the detailed description, unless otherwise described or provided, the same drawing reference numerals may be understood to refer to the same or like elements, features, and structures. The drawings may not be to scale, and the relative size, proportions, and depiction of elements in the drawings may be exaggerated for clarity, illustration, and convenience.

DETAILED DESCRIPTION

The following detailed description is provided to assist the reader in gaining a comprehensive understanding of the methods, apparatuses, and/or systems described herein. However, various changes, modifications, and equivalents of the methods, apparatuses, and/or systems described herein will be apparent after an understanding of the disclosure of this application. For example, the sequences of operations described herein are merely examples, and are not limited to those set forth herein, but may be changed as will be apparent after an understanding of the disclosure of this application, with the exception of operations necessarily occurring in a certain order. Also, descriptions of features that are known after an understanding of the disclosure of this application may be omitted for increased clarity and conciseness.

The features described herein may be embodied in different forms and are not to be construed as being limited to the examples described herein. Rather, the examples described herein have been provided merely to illustrate some of the many possible ways of implementing the methods, apparatuses, and/or systems described herein that will be apparent after an understanding of the disclosure of this application. The use of the term "may" herein with respect to an example or embodiment, e.g., as to what an example or embodiment may include or implement, means that at least one example or embodiment exists where such a feature is included or implemented, while all examples are not limited thereto.

The terminology used herein is for describing various examples only and is not to be used to limit the disclosure. The articles "a," "an," and "the" are intended to include the plural forms as well, unless the context clearly indicates otherwise. As non-limiting examples, terms "comprise" or "comprises," "include" or "includes," and "have" or "has" specify the presence of stated features, numbers, operations, members, elements, and/or combinations thereof, but do not preclude the presence or addition of one or more other features, numbers, operations, members, elements, and/or combinations thereof, or the alternate presence of an alternative stated features, numbers, operations, members, elements, and/or combinations thereof. Additionally, while one embodiment may set forth such terms "comprise" or "comprises," "include" or "includes," and "have" or "has" specify the presence of stated features, numbers, operations, members, elements, and/or combinations thereof, other embodiments may exist where one or more of the stated features, numbers, operations, members, elements, and/or combinations thereof are not present.

As used herein, the term "and/or" includes any one and any combination of any two or more of the associated listed items. The phrases "at least one of A, B, and C", "at least one of A, B, or C", and the like are intended to have disjunctive meanings, and these phrases "at least one of A, B, and C", "at least one of A, B, or C", and the like also include examples where there may be one or more of each of A, B, and/or C (e.g., any combination of one or more of each of A, B, and C), unless the corresponding description and embodiment necessitates such listings (e.g., "at least one of A, B, and C") to be interpreted to have a conjunctive meaning.

Throughout the specification, when a component or element is described as being "connected to," "coupled to," or "joined to" another component or element, it may be directly "connected to," "coupled to," or "joined to" the other component or element, or there may reasonably be one or more other components or elements intervening therebetween. When a component or element is described as being "directly connected to," "directly coupled to," or "directly joined to" another component or element, there can be no other elements intervening therebetween. Likewise, expressions, for example, "between" and "immediately between" and "adjacent to" and "immediately adjacent to" may also be construed as described in the foregoing. It is to be understood that if a component (e.g., a first component) is referred to, with or without the term "operatively" or "communicatively," as "coupled with," "coupled to," "connected with," or "connected to" another component (e.g., a second component), it means that the component may be coupled with the other component directly (e.g., by wire), wirelessly, or via a third component.

Although terms such as "first," "second," and "third", or A, B, (a), (b), and the like may be used herein to describe various members, components, regions, layers, or sections, these members, components, regions, layers, or sections are not to be limited by these terms. Each of these terminologies is not used to define an essence, order, or sequence of corresponding members, components, regions, layers, or sections, for example, but used merely to distinguish the corresponding members, components, regions, layers, or sections from other members, components, regions, layers, or sections. Thus, a first member, component, region, layer, or section referred to in the examples described herein may also be referred to as a second member, component, region, layer, or section without departing from the teachings of the examples.

Unless otherwise defined, all terms, including technical and scientific terms, used herein have the same meaning as commonly understood by one of ordinary skill in the art to which this disclosure pertains and based on an understanding of the disclosure of the present application. Terms, such as those defined in commonly used dictionaries, are to be interpreted as having a meaning that is consistent with their meaning in the context of the relevant art and the disclosure of the present application and are not to be interpreted in an idealized or overly formal sense unless expressly so defined herein.

FIG. 1 illustrates an example computing device that may be configured to perform cell analysis according to one or more embodiments. Referring to FIG. 1, a computing device 100 may include an electrode layer 110, an interposer layer 130, a circuit layer 150, and a controller 170.

The electrode layer 110 may include a plurality of microelectrode arrays (MEAs) 115, and each MEA may be configured with electrodes arranged in a determined pattern (e.g., electrodes 415 of FIG. 4) for stimulation and sensing of cells. For example, the electrode array 110 may be packaged to be waterproof. The cells may include, for example, nerve cells, such as neurons and/or brain nerve cells, but are not necessarily limited thereto. The cells may generate at least one of an electrical signal, an optical signal, and a chemical signal, through nerve stimulation by the electrodes of the MEAs 115. The cells may be cultured in a cell culture vessel as a non-limiting example.

In an example, the computing device 100 may further include the cell culture vessel containing a cell culture medium that cultures the cells. The electrode layer 110 and the cell culture vessel may be disposed adjacent to each other. The plurality of MEAs 115 of the electrode layer 110 may stimulate the cells cultured in the cell culture vessel, sense excitement of the cells by the stimulation, and transmit the excitement of the cells to a plurality of circuit chips 155 of the circuit layer 150, respectively.

In an example, spatial efficiency may be improved by flip-chip bonding the plurality of circuit chips 155 by a three-dimensional (3D) structure in which the electrode layer 110 and the circuit layer 150 to which the cells are attached are physically separated in chip units. The "flip-chip bonding" may be, instead of wire bonding that connects a chip to a substrate with a wire in a process of connecting the chip to the substrate with metal for the electrical properties of semiconductors, a method of attaching a ball (e.g., a solder ball) directly to the substrate and mounting the chip on a package after the chip is flipped. The solder ball may also be referred to as a "solder bump". The solder ball may connect, for example, the substrate to a main printed circuit board (PCB).

In an example, by composing the electrode layer 110 and the circuit layer 150 separately, the number of electrodes used in each of the plurality of MEAs 115 may increase and used in an optimized manner, and at least one of the plurality of circuit chips 155 may be reused to implement a scalable recording system (e.g., a computing device). For example, when the electrodes (e.g., N electrodes) of an MEA corresponding to one circuit chip {1, 1} are connected, as shown in a rear portion 250 of FIG. 2, {N, N} electrodes may be bonded to one circuit chip. Here, as the number of circuit chips increases, the number of electrodes that may be used by being connected to the circuit chips may also increase in proportion. For example, when two or three circuit chips are connected, the number of electrodes may also double or triple in proportion to the number of connected circuit chips.

As the number of electrodes for sensing signals of the cells increases, the number of electrodes to record, interpret, or analyze the sensed signals increases proportionally, and accordingly, the amount of data to be analyzed at once may increase. In this case, the computing device 100 may schedule an order of activating the circuit chips and/or may selectively store the signals of the cells by prioritizing the electrodes that activate the circuit chips. In addition, a process may be facilitated by making the plurality of MEAs 115 of the electrode layer 110 into separate chips.

For example, the electrode layer 110 may be formed on one side of a substrate on which the interposer layer 130 is formed. In this case, the circuit layer 150 may be formed on the same one side of the substrate on which the interposer layer 130 is formed, or may be formed on an opposing side, namely, the other side of the substrate.

The interposer layer 130 may include an interposer for a wiring connection between the plurality of MEAs 115 and the substrate. The substrate may include, for example, one of a PCB and a silicon substrate, but is not necessarily limited thereto.

The interposer layer 130 may have, for example, a multilayer wiring structure for redistributing an input/output (I/O) of an integrated circuit (IC) and may include a via to implement the multilayer wiring structure. The form of the via may include a through hole, a blind via, a buried via, and the like. The via may serve as a connector for electrical conduction between layers. For example, when routing between electrodes and a sensor circuit is determined as being long, the area of the sensor circuit may be configured to be the same as the area of the electrodes, thereby solving a potential severe deviation of signals due to the routing through a through silicon via (TSV).

The interposer of the interposer layer 130 may be at least one of a silicon interposer, a glass interposer, and an organic interposer as non-limiting examples.

In an example, the silicon interposer may be configured by attaching a die including the IC to a high-density silicon interposer in a flip-chip form and then attaching the silicon interposer to a ball grid array (BGA) substrate in the flip-chip form. In the organic interposer, a redistributed layer (RDL) may be responsible for a high-density interconnection between a plurality of dies. The glass interposer may be composed of glass. The glass may have excellent electrical properties as an insulator and have little electrical loss at high frequencies. When the interposer layer 130 includes such a glass interposer, a culture state of the cells may be easily checked.

The electrode layer 110 and the interposer layer 130 may be configured as one layer on one wafer or may be configured separately from each other, as non-limiting examples.

For example, when the electrode layer 110 and the interposer layer 130 are configured as one layer, the interposer layer 130, the electrode layer 110, and the circuit layer 150 may be connected to each other by the flip-chip bonding.

Alternatively, the electrode layer 110 may be configured as a silicon wafer and the interposer layer 130 may be configured as a PCB, separately. In this case, the electrode layer 110, the interposer layer 130, and the circuit layer 150 may be also connected to each other by the flip-chip bonding.

For example, when the substrate is a silicon substrate, the interposer layer 130 may include the electrode layer 110 and may be thus configured as a silicon interposer formed on the silicon substrate.

In an example, a chip bonding may be selected by designing a routing pattern of the interposer layer 130 in any suitable way, so examples include the plurality of MEAs 115 of the electrode layer 110 being arranged in various expandable forms.

An arrangement relationship between the electrode layer 110, the interposer layer 130, and the circuit layer 150 will be described in more detail with reference to FIGS. 2 and 3 below.

The circuit layer 150 may include the plurality of circuit chips 155, each of which may be configured to stimulate the cells and record the excitement of the cells by the stimulation.

In an example, the circuit layer 150 may include at least one of an analog front-end (AFE) that may be configured to stimulate the cells and record the excitement of the cells by the stimulation in the form of an electrical signal, and a digital baseband that is configured to perform signal processing for the electrical signal.

The AFE may amplify an output of a sensor that detects the excitement of the cells through an amplifier, convert a signal having waveform adjusted through a filter into a digital signal through an analog-to-digital converter (ADC), and transmit the digital signal. The AFE may include one side that may be connected to a radio frequency (RF) antenna, and the other side that may be connected to digital-to-analog converter (DAC)/ADC converters, as a non-limiting example. The AFE may be connected to the controller 170.

The AFE may include, for example, a stimulator for stimulating the cells, a signal amplifier for amplifying a signal sensed by the cells, and/or an ADC for converting the amplified (analog) signal into a digital signal, but is not necessarily limited thereto.

A digital baseband may perform the signal processing on the electrical signal of the cells converted into the digital signal in the ADC as a non-limiting example.

The controller 170 may include one or more processors configured to execute instructions, one or more memories storing the instructions, and the execution of the instructions by the one or more processors may configure the controller to control any one or any combination of operations described herein. The controller 170 may also be a hardware, any processing device, or circuitry.

In an example, the controller 170 may control whether to connect the plurality of MEAs 115 to the plurality of circuit chips 155, respectively. The controller 170 may determine whether to connect the plurality of circuit chips 155 to the plurality of MEAs 115, respectively, based on at least one of the number and position(s) of the electrodes used for the stimulation and the sensing of the cells.

The controller 170 may determine the number and position(s) of circuit chips used among the plurality of circuit chips 155, based on at least one of the number and the position(s) of the electrodes used for the stimulation and the sensing of the cells.

The controller 170 may selectively use the electrodes in an area corresponding to the position(s) of the cells to be measured in the plurality of MEAs 115 in association with whether the plurality of respective circuit chips 155 are activated. The circuit chips 155 may be activated to stimulate cells (e.g., brain nerve cells) by injecting current through the electrodes of the plurality of MEAs 115. A cell analysis device (e.g., the computing device 100) may analyze the cells by detecting excitation of the cells by a stimulus.

The controller 170 may selectively use the electrodes corresponding to the respective activated circuit chips in the plurality of MEAs 115 in response to the activation of the plurality of circuit chips 155. The controller 170 may also select the electrodes of one MEA corresponding to one activated circuit chip, or may also select the electrodes of the plurality of MEAs 115 corresponding to one activated circuit chip, in response to the activation of the one circuit chip. Here, the electrodes corresponding to the activated circuit chips may be the electrodes positioned adjacent to each other in one MEA corresponding to the respective activated circuit chips, may be the electrodes spaced apart from each other in one MEA corresponding to the respective activated circuit chips, or may be the electrodes spaced apart from each other in the plurality of MEAs 115 corresponding to the respective activated circuit chips.

Regardless of the number of electrodes, the controller 170 may implement a structure effective and suitable for measuring large-scale cells by intensively activating the electrodes at any suitable positions.

The number and the arrangement of the electrodes used in the plurality of MEAs 115 may be determined based on the bonding position(s) and the number of circuit chips 155. The controller 170 may select and activate the circuit chip in which the bonding position of the plurality of circuit chips 155 in the circuit layer 150 corresponds to the position of the cells to be measured. In addition, the controller 170 may determine the number and the arrangement of the activated electrodes to match the arrangement of the cells to be measured. A method of selectively using the electrodes by the controller 170 is described in more detail with reference to FIGS. 4 and 5 below.

Figure 2:
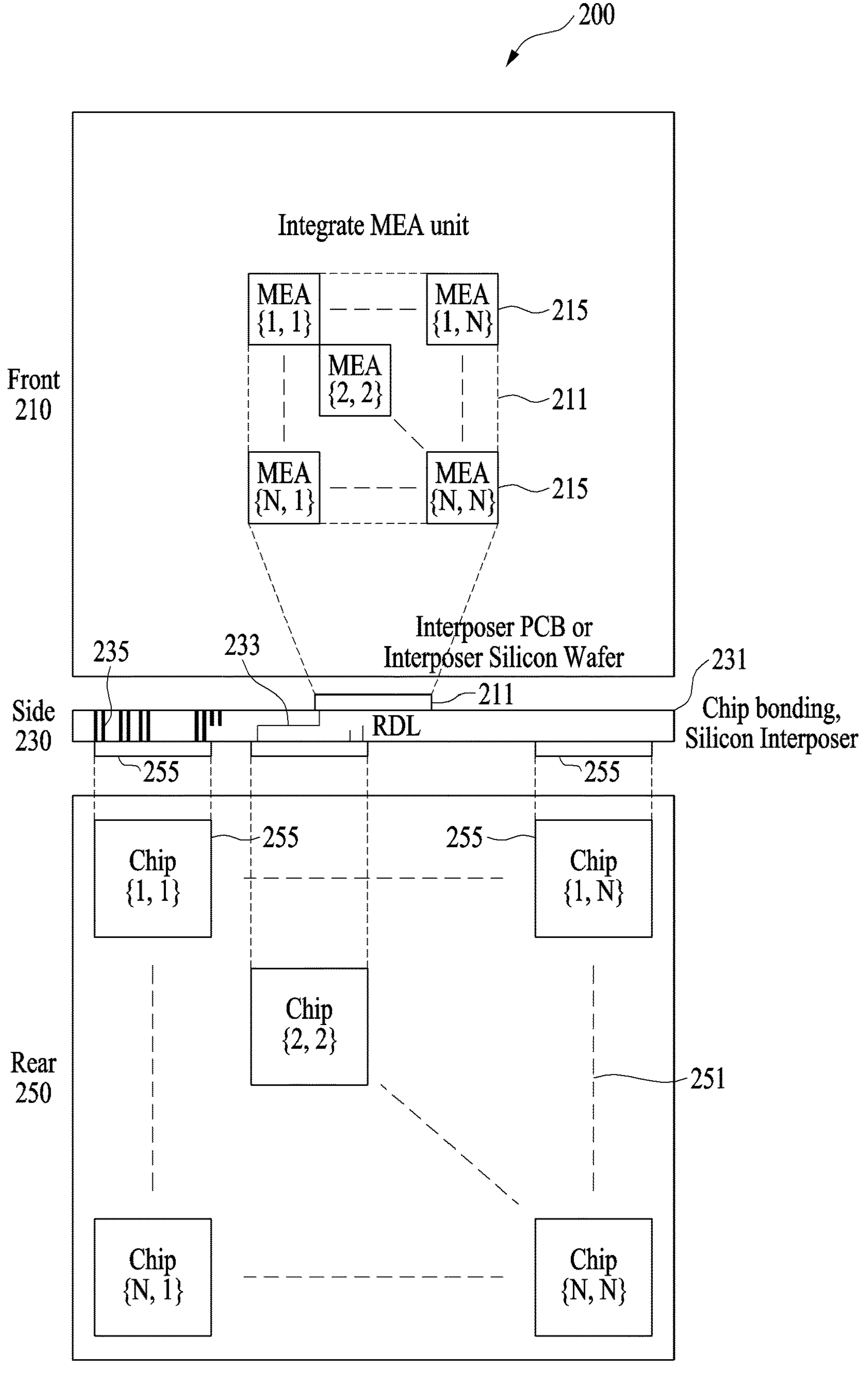
FIG. 2 illustrates an example arrangement relationship between an electrode layer, an interposer layer, and a circuit layer according to one or more embodiments.

FIG. 2 illustrates an example configuration of a computing device and an example arrangement relationship between an electrode layer, an interposer layer, and a circuit layer of the computing device according to one or more embodiments. Referring to FIG. 2, a computing device 200 (e.g., the computing device 100 in FIG. 1) may be configured with a front portion 210, a side portion 230, and a rear portion 250 as a non-limiting example.

In an example, the front portion 210 may include an electrode layer 211 configured with a plurality of MEAs 215 that may be disposed on a front surface of the computing device 200. The plurality of MEAs 215 may be packaged in a center of a substrate of the computing device 200 by centrally integrated electrode pads. For example, the packaging of the electrodes may be performed by maintaining a form by the centrally integrated electrode pads for efficiency. Here, the sizes of the plurality of MEAs 215 may be the same or different from each other. When the sizes of the plurality of MEAs 215 are the same, since the conductivities of the signals sensed from the cells are the same, the sizes of the sensing signals may be maintained the same. When the sizes of the plurality of MEAs 215 are different from each other, since the conductivities of the signals sensed from the cells are different, the sizes of the sensing signals may vary.

In an example, the side portion 230 may include an interposer layer 231 in which an RDL 233 and a TSV 235 may be disposed. The interposer layer 231 may be configured to connect the electrode layer 211 to a circuit layer 251 of the computing device 200. The RDL 233 may be configured to change a wiring position to an edge of a chip die to facilitate packaging of a pad, which is an I/O terminal of a chip. By using the RDL 233 instead of directly bonding wires to the pad at the center of the chip, the routing of the wiring may be freed as a non-limiting example.

In examples, by composing a silicon chip in which the electrode layer 211 and the interposer layer 231 are combined in any suitable forms, examples include the usable number and the form of the electrodes being diversified according to bonding position(s) and the number of circuit layers 251.

In an example, the rear portion 250 may include the circuit layer 251 configured with a plurality of circuit chips 255 that may be disposed on a rear surface of the computing device 200. Examples include the plurality of circuit chips 255 being bonded in any suitable ways without being limited to type or size.

The type and the size of the plurality of circuit chips 255 may be the same or different from each other. As non-limiting examples, a first circuit chip among the plurality of circuit chips 255 may correspond to a high-performance AFE chip and a second circuit chip may correspond to a high-integration AFE chip. In addition, the first circuit chip may support "1000" electrodes or a third circuit chip may support "1500" electrodes, as non-limiting examples.

In an example, the plurality of circuit chips 255 may be arranged as respective pads formed on the rear surface of the computing device 200. These pads of the plurality of circuit chips may be connected by forming the respective pads on the interposer layer 231 in advance and bonding each pad of the plurality of circuit chips 255 to a corresponding pad of the interposer layer 231 using a die-to-die flip-chip. Here, the number and the positions of the plurality of circuit chips 255 may be basically matched with the respective positions of the electrodes of the plurality of MEAs 215 on the front surface of the computing device 200, and a controller (e.g., the controller 170 of FIG. 1) may thus select matched ones from the circuit chips 255 according to the number of the required electrodes.

Here, an electrode pad for the plurality of MEAs 215 may be disposed on the interposer layer 231 or on an upper portion of the silicon substrate on which the interposer layer 231 is positioned. In addition, a bonding pad for the plurality of circuit chips 255 may be disposed on the upper portion or a lower portion of the silicon substrate. For example, when the plurality of circuit chips 255 are disposed facing the plurality of MEAs 215 with respect to the interposer layer 231 as shown in FIG. 2, the bonding pad for the plurality of circuit chips 255 may be disposed on the lower portion of the silicon substrate. In contrast, when a plurality of circuit chips 355 is disposed on the same plane as a plurality of MEAs 315 as shown in FIG. 3 below, a bonding pad for the plurality of circuit chips 355 may be disposed on the upper portion of the silicon substrate like the electrode pad for the plurality of MEAs 315.

Whether to connect the plurality of circuit chips 255 to the plurality of respective MEAs 215 may be determined based on at least one of the number and the positions of the electrodes used for the stimulation and the sensing of the cells. In addition, the number and the positions of the circuit chips used among the plurality of circuit chips 255 may be determined based on at least one of the number and the positions of the respective electrodes used for the stimulation and the sensing of the cells.

As a non-limiting example, the number of MEAs 215 may be the same as the number of circuit chips 255. For example, when the number of MEAs 215 is N, the number of circuit chips 255 may also be N.

The plurality of circuit chips 255 and the plurality of MEAs 215 may be matched one-to-one. For example, a chip {1, 1} among the plurality of circuit chips 255 disposed on the rear surface of the computing device 200 may match with an MEA {1, 1} disposed on the front surface of the computing device 200 and a chip {2, 2} disposed on the rear surface may match with an MEA {2, 2} disposed on the front surface of the computing device 200.

In response to whether the circuit chips corresponding to the electrodes are activated in the plurality of circuit chips 255, the electrodes of the plurality of MEAs 215 may flexibly determine whether to use the circuit chips, as a non-limiting example.

Even though the positions of the plurality of circuit chips 255 disposed on the rear surface of the computing device 200 are fixed, internal wiring of the interposer layer 231 may be freely designed, and accordingly, the controller 170 may select the positions and the forms of the electrodes of the plurality of MEAs 215 for an optimized operation. Thus, the electrodes of the plurality of MEAs 215 may be intensively disposed or activated at the desired positions regardless of the number of electrodes, so that a structure advantageous for measuring large-scale cells may be formed.

In an example, the electrodes of the plurality of MEAs 215 may be configured with various forms by forming a wiring structure of the interposer layer 231 in respective ways.

Alternatively, the plurality of circuit chips 255 and the plurality of MEAs 215 may be matched one-to-many. As a non-limiting example, the chip {1, 1} among the plurality of circuit chips 255 disposed on the rear surface may match at least a portion of electrodes of the MEA {1, 1} disposed on the front surface of the computing device 200, at least a portion of electrodes of an MEA {1, 2}, and at least a portion of electrodes of the MEA {2, 2}.

The matching between the plurality of circuit chips 255 and the plurality of MEAs 215 is described in more detail with reference to FIGS. 4 and 5 below.

The electrode layer 211 may be formed on one side of the silicon substrate on which the interposer layer 231 is formed, and the circuit layer 251 may be formed on the other side of the silicon substrate on which the interposer layer 231 is formed. As a non-limiting example, the electrode layer 211 and the interposer layer 231 may be connected by flip-chip bonding by at least one of a micro bump and, a TSV having a fine line width (e.g., $<1$ micrometer (μm) or $<2$ μm). On the other hand, the plurality of circuit chips 255 of the circuit layer 251 and the interposer layer 231 may be connected to each other by at least one of a micro bump, an RDL, and a TSV having a fine line width, but is not necessarily limited thereto.

Figure 3:
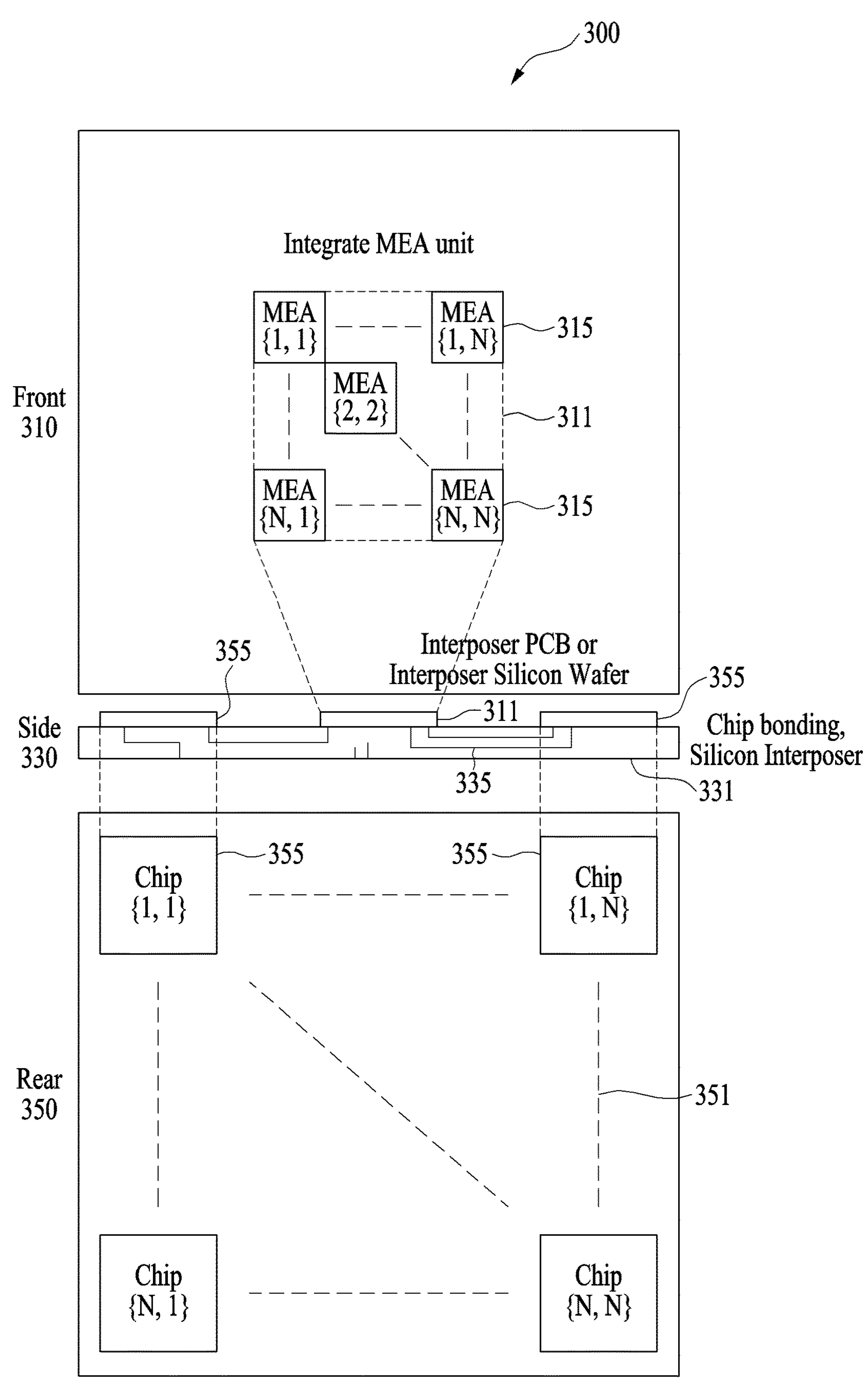
FIG. 3 illustrates an example arrangement relationship between an electrode layer, an interposer layer, and a circuit layer according to one or more embodiments.

FIG. 3 illustrates an example arrangement relationship between an electrode layer, an interposer layer, and a circuit layer of a computing device according to one or more embodiments. Referring to FIG. 3, the computing device (e.g., the computing device 100 in FIG. 1 or 200 in FIG. 2) may be configured with a front portion 310, a side portion 330, and a rear portion 350.

In an example, the front portion 310 may include an electrode array 311 with a plurality of MEAs 315 that may be disposed on a front surface of the computing device 300.

In an example, the side portion 330 may include an interposer layer 331 in which an RDL 335 may be disposed. The interposer layer 331 may be configured to connect the electrode layer 311 to a circuit layer 351.

In an example, the rear portion 350 may include the circuit layer 351 configured with a plurality of circuit chips 355 that may be disposed on a rear surface of the computing device 300.

Here, the electrode layer 311 may be formed on one side of the silicon substrate on which the interposer layer 331 is formed and the circuit layer 351 may be formed on the same one side of the silicon substrate as a non-limiting example.

The interposer layer 331 may include the RDL 335, and electrodes of the plurality of MEAs 315 may be connected to the plurality of circuit chips 355 through the RDL 335. The RDL 335 may be made of a metal material, for example, copper, gold, or an aluminum alloy, but is not necessarily limited thereto.

Figure 4:
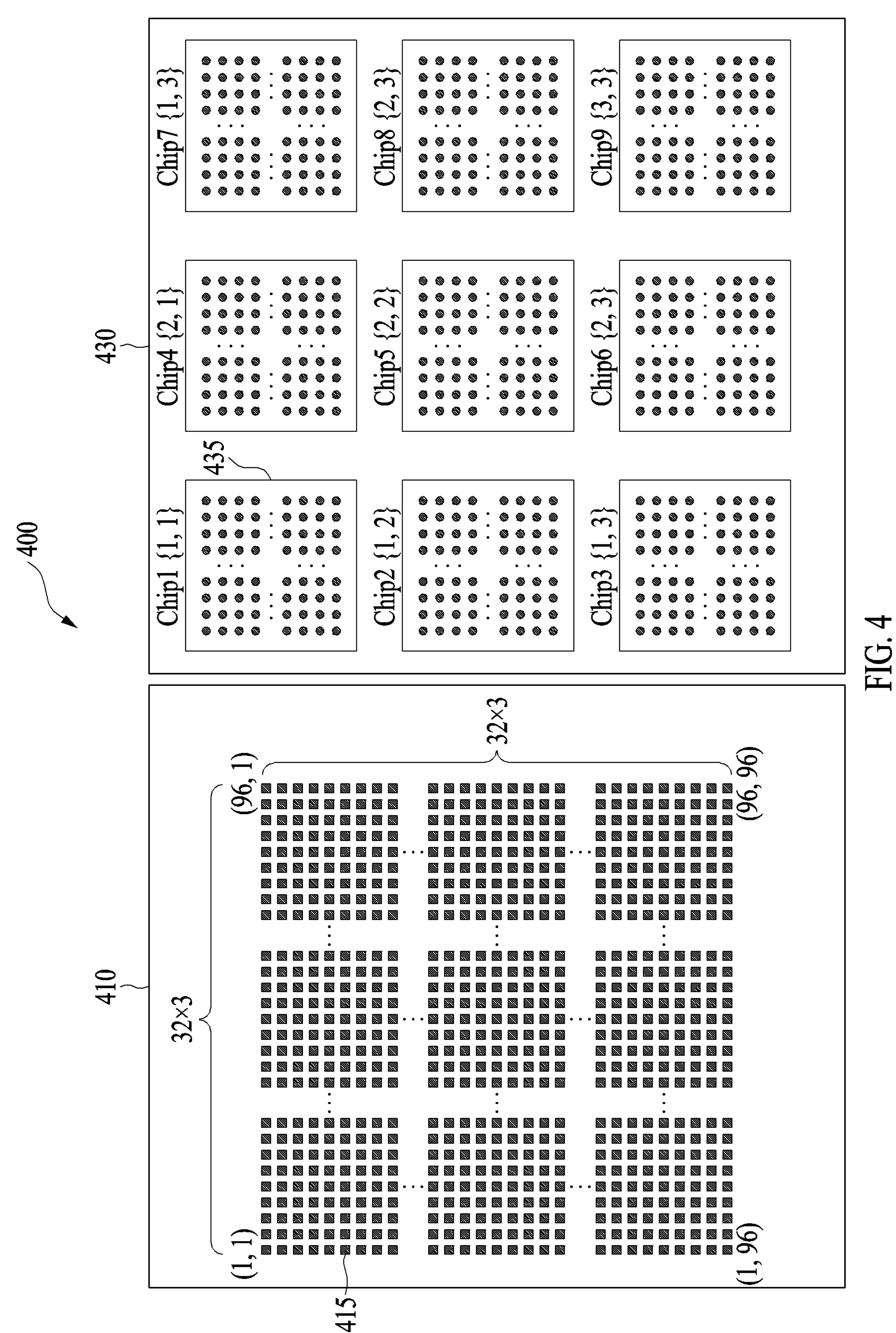
FIG. 4 illustrates an example arrangement of a plurality of microelectrode arrays (MEAs) and a plurality of circuit chips according to one or more embodiments.

FIG. 4 illustrates an example arrangement of the plurality of MEAs and the plurality of circuit chips of a computing device according to one or more embodiments. Referring to FIG. 4, an example computing device (e.g., the computing device 100, 200 or 300, or any combination thereof, as non-limiting examples) may include an example configuration 400 in which electrodes 415 of MEAs are activated in correspondence to the plurality of circuit chips.

As described above, the number of MEAs may correspond to the number of circuit chips, and thus as illustrated in FIG. 4, the computing device may include, for example, a plurality of circuit chips 430 (e.g., "9") corresponding to a plurality of MEAs 410 (e.g., "9").

One MEA may include a total of (32×32) "1024" electrodes 415. In addition, the plurality of circuit chips 430 may include the total of "9" circuit chips, from circuit chip 1 {1, 1} 435 through circuit chip 9 {3, 3}.

In an example, the electrode pads for the "9" MEAs 410 may be disposed on an interposer layer (e.g., the interposer layer 231 in FIG. 2 or 331 in FIG. 3) or on an upper portion of a substrate of the computer device. The plurality of MEAs 410 may be packaged on the substrate by the centrally integrated electrode pads.

The bonding pads for the "9" circuit chips 430 may be disposed a lower portion of the substrate. The bonding pad may also be referred to as an I/O pad.

The circuit chip 1 {1, 1} 435 among the "9" circuit chips 430 may match with an MEA positioned first among the plurality of MEAs 410 as a non-limiting example.

The computing device may activate up to (32×3)×(32×3) ="9216" electrodes using the "9" circuit chips 430. A pattern of the electrodes activated by matching to the respective activated circuit chips is described in more detail with reference to FIG. 5 below.

Figure 5:
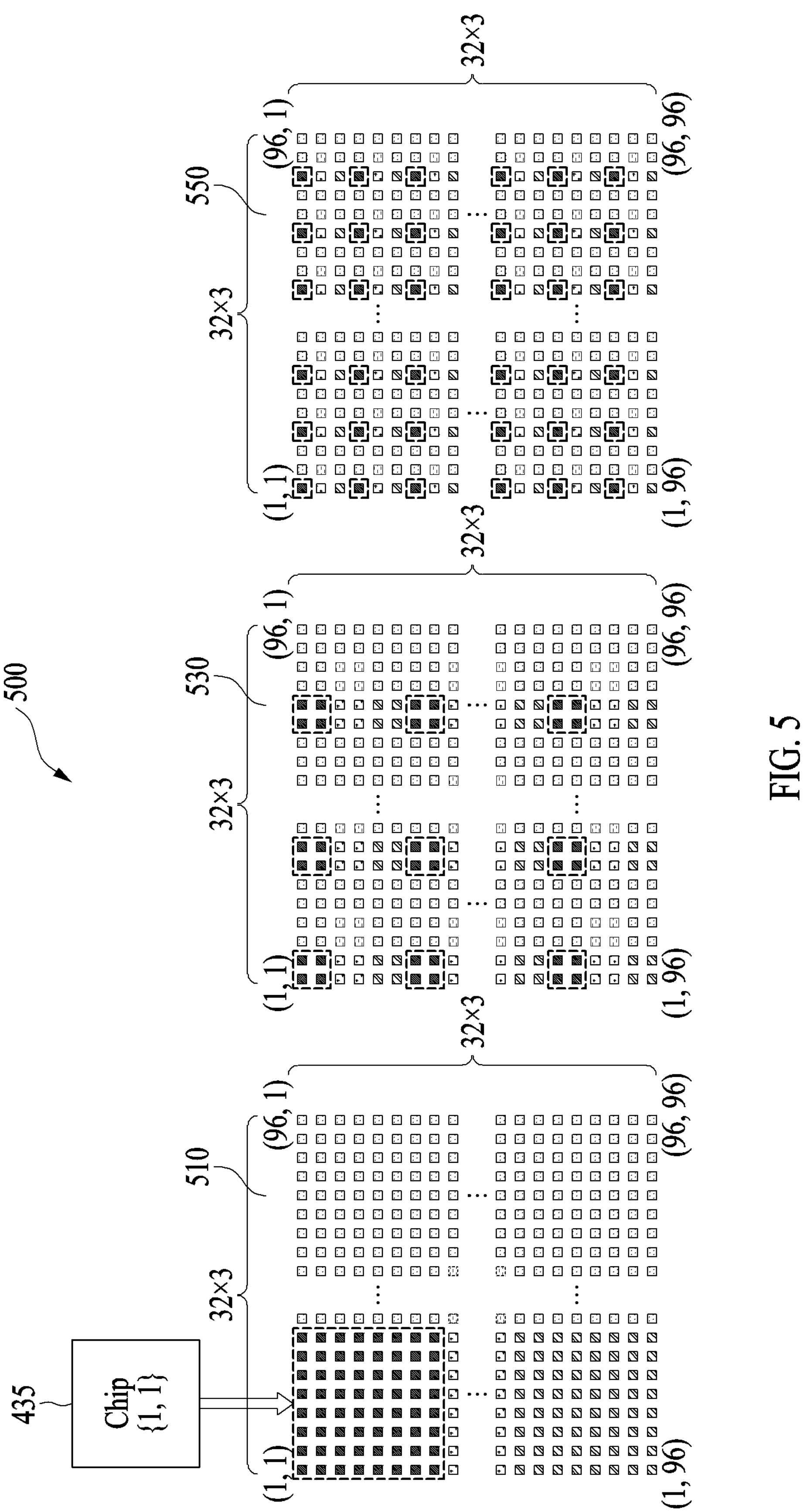
FIG. 5 illustrates an example pattern of electrodes activated by circuit chips according to one or more embodiments.

FIG. 5 illustrates an example pattern of the electrodes activated by the circuit chips according to one or more embodiments. Referring to FIG. 5, an example pattern 500 illustrates configurations 510, 530 and 550 in which the electrodes of the plurality of MEAs are activated by the circuit chip 1 {1, 1} 435, for example, among the plurality of the circuit chips.

As shown in the configuration 510, the circuit chip 1 {1, 1} 435 may be activated and use the electrodes positioned adjacent to each other in one MEA corresponding to the activated circuit chip 1 {1, 1} 435.

Specifically, as shown in the configuration 510, when the cells to be observed concentrate in one area, the computing device may stimulate the cells by activating the electrodes positioned adjacent to each other in one MEA corresponding to an area where the cells are gathered corresponding to the circuit chip 1 {1, 1} 435 and may detect the excitement of the cells by the stimulation.

Alternatively, as shown in the configuration 530 or 550, when the cells to be observed are spread over a wide area at regular intervals, the computing device may activate the electrodes by grouping the electrodes positioned spaced apart from each other in one or more MEAs corresponding to an area where the cells are spread corresponding to the circuit chip 1 {1, 1} 435 or may stimulate the cells by activating each of the electrodes spaced apart from each other in the plurality of MEAs. The computing device may detect the excitation of the cells by the stimulation. Here, the electrodes spaced apart from each other may be disposed at regular intervals or grouped at regular intervals, as non-limiting examples.

In an example, a desired pattern of the electrodes may be implemented through the RDL of the interposer layer (e.g., the interposer layer 231 in FIG. 2 or 331 in FIG. 3). For example, when manufacturing the computing device, an interposer may be manufactured in various patterns because there is no restriction on the fine line width process, and the pattern and the number of electrodes may be adjusted by flip-chip bonding the number of circuit chips. In this way, the electrodes may be intensively disposed at the desired positions regardless of the number of electrodes, thereby improving or optimizing the measuring of the large-scale cells.

In an example, the MEA including the electrodes and the plurality of circuit chips may be physically separated to increase the degree of integration of the electrodes, thereby maximizing the number of the electrodes to be used by the computing device.

The processors, memories, computing devices, and other apparatuses, devices, and components described herein with respect to FIGS. 1-5 are implemented by or representative of hardware components. Examples of hardware components that may be used to perform the operations described in this application where appropriate include controllers, sensors, generators, drivers, memories, comparators, arithmetic logic units, adders, subtractors, multipliers, dividers, integrators, and any other electronic components configured to perform the operations described in this application. In other examples, one or more of the hardware components that perform the operations described in this application are implemented by computing hardware, for example, by one or more processors or computers. A processor or computer may be implemented by one or more processing elements, such as an array of logic gates, a controller and an arithmetic logic unit, a digital signal processor, a microcomputer, a programmable logic controller, a field-programmable gate array, a programmable logic array, a microprocessor, or any other device or combination of devices that is configured to respond to and execute instructions in a defined manner to achieve a desired result. In one example, a processor or computer includes, or is connected to, one or more memories storing instructions or software that are executed by the processor or computer. Hardware components implemented by a processor or computer may execute instructions or software, such as an operating system (OS) and one or more software applications that run on the OS, to perform the operations described in this application. The hardware components may also access, manipulate, process, create, and store data in response to execution of the instructions or software. For simplicity, the singular term "processor" or "computer" may be used in the description of the examples described in this application, but in other examples multiple processors or computers may be used, or a processor or computer may include multiple processing elements, or multiple types of processing elements, or both. For example, a single hardware component or two or more hardware components may be implemented by a single processor, or two or more processors, or a processor and a controller. One or more hardware components may be implemented by one or more processors, or a processor and a controller, and one or more other hardware components may be implemented by one or more other processors, or another processor and another controller. One or more processors, or a processor and a controller, may implement a single hardware component, or two or more hardware components. A hardware component may have any one or more of different processing configurations, examples of which include a single processor, independent processors, parallel processors, single-instruction single-data (SISD) multiprocessing, single-instruction multiple-data (SIMD) multiprocessing, multiple-instruction single-data (MISD) multiprocessing, and multiple-instruction multiple-data (MIMD) multiprocessing.

The methods illustrated in FIGS. 1-5 that perform the operations described in this application are performed by computing hardware, for example, by one or more processors or computers, implemented as described above implementing instructions or software to perform the operations described in this application that are performed by the methods. For example, a single operation or two or more operations may be performed by a single processor, or two or more processors, or a processor and a controller. One or more operations may be performed by one or more processors, or a processor and a controller, and one or more other operations may be performed by one or more other processors, or another processor and another controller. One or more processors, or a processor and a controller, may perform a single operation, or two or more operations.

Instructions or software to control computing hardware, for example, one or more processors or computers, to implement the hardware components and perform the methods as described above may be written as computer programs, code segments, instructions or any combination thereof, for individually or collectively instructing or configuring the one or more processors or computers to operate as a machine or special-purpose computer to perform the operations that are performed by the hardware components and the methods as described above. In one example, the instructions or software include machine code that is directly executed by the one or more processors or computers, such as machine code produced by a compiler. In another example, the instructions or software includes higher-level code that is executed by the one or more processors or computer using an interpreter. The instructions or software may be written using any programming language based on the block diagrams and the flow charts illustrated in the drawings and the corresponding descriptions herein, which disclose algorithms for performing the operations that are performed by the hardware components and the methods as described above.

The instructions or software to control computing hardware, for example, one or more processors or computers, to implement the hardware components and perform the methods as described above, and any associated data, data files, and data structures, may be recorded, stored, or fixed in or on one or more non-transitory computer-readable storage media. Examples of a non-transitory computer-readable storage medium include read-only memory (ROM), random-access programmable read only memory (PROM), electrically erasable programmable read-only memory (EEPROM), random-access memory (RAM), dynamic random access memory (DRAM), static random access memory (SRAM), flash memory, non-volatile memory, CD-ROMs, CD-Rs, CD+Rs, CD-RWs, CD+RWs, DVD-ROMs, DVD-Rs, DVD+Rs, DVD-RWs, DVD+RW, DVD-RAMs, BD-ROMs, BD-Rs, BD-R LTHs, BD-REs, blue-ray or optical disk storage, hard disk drive (HDD), solid state drive (SSD), flash memory, a card type memory such as multimedia card micro or a card (for example, secure digital (SD) or extreme digital (XD)), magnetic tapes, floppy disks, magneto-optical data storage devices, optical data storage devices, hard disks, solid-state disks, and any other device that is configured to store the instructions or software and any associated data, data files, and data structures in a non-transitory manner and provide the instructions or software and any associated data, data files, and data structures to one or more processors or computers so that the one or more processors or computers can execute the instructions. In one example, the instructions or software and any associated data, data files, and data structures are distributed over network-coupled computer systems so that the instructions and software and any associated data, data files, and data structures are stored, accessed, and executed in a distributed fashion by the one or more processors or computers.

While this disclosure includes specific examples, it will be apparent after an understanding of the disclosure of this application that various changes in form and details may be made in these examples without departing from the spirit and scope of the claims and their equivalents. The examples described herein are to be considered in a descriptive sense only, and not for purposes of limitation. Descriptions of features or aspects in each example are to be considered as being applicable to similar features or aspects in other examples. Suitable results may be achieved if the described techniques are performed in a different order, and/or if components in a described system, architecture, device, or circuit are combined in a different manner, and/or replaced or supplemented by other components or their equivalents.

Therefore, in addition to the above disclosure, the scope of the disclosure may also be defined by the claims and their equivalents, and all variations within the scope of the claims and their equivalents are to be construed as being included in the disclosure.

What is claimed is:

1. A computing device comprising:

an electrode layer comprising a plurality of microelectrode arrays (MEAs), each MEA being configured with electrodes for stimulation and sensing of biological cells;

an interposer layer comprising an interposer for a wiring connection between the plurality of MEAs and a substrate of the computing device;

a circuit layer comprising a plurality of circuit chips configured to stimulate the cells and store excitement of the cells in response to the stimulation by corresponding electrodes; and a controller configured to control whether or how to connect the plurality of circuit chips to the plurality of MEAs.

2. The computing device of claim 1, wherein the interposer layer comprises the electrode layer with the interposer layer and the circuit layer being connected to each other by flip-chip bonding.

3. The computing device of claim 1, wherein the electrode layer is formed on one side of the substrate on which the interposer layer is formed, and wherein the circuit layer is formed on the one side of the substrate or on an opposing side of the substrate.

4. The computing device of claim 1, wherein the controller is configured to determine whether or how to connect the plurality of circuit chips to the plurality of respective MEAs, based on at least one of a number of the electrodes used for the stimulation and the sensing of the cells, or based on positions of the electrodes used for the stimulation.

5. The computing device of claim 1, wherein the controller is configured to select a number of circuit chips used among the plurality of circuit chips and determine positions of the selected circuit chips, based on at least one of a number of the electrodes used for the stimulation and the sensing of the cells, or positions of the electrodes used for the stimulation.

6. The computing device of claim 1, wherein, based on whether the plurality of circuit chips are activated, the controller is configured to selectively use electrodes corresponding to an activated circuit chip among the plurality of MEAs.

7. The computing device of claim 6, wherein the electrodes corresponding to the activated circuit chip comprise at least one of:

electrodes positioned adjacent to each other in one MEA corresponding to the activated circuit chip;

electrodes spaced apart from each other in one MEA corresponding to the activated circuit chip; and electrodes spaced apart from each other in a plurality of MEAs corresponding to the activated circuit chip.

8. The computing device of claim 1, wherein a number of the electrodes used for stimulation and an arrangement of the electrodes for the stimulation are determined based on bonding positions of corresponding circuit chips and a number of the corresponding circuit chips.

9. The computing device of claim 1, wherein the plurality of MEAs is packaged on the substrate by centrally integrated electrode pads.

10. The computing device of claim 1, wherein sizes of at least some of the plurality of MEAs are same or different from each other.

11. The computing device of claim 1, wherein respective types and sizes of at least some of the plurality of circuit chips are same or different from each other.

12. The computing device of claim 1, wherein the electrode layer and the interposer layer are connected by flip-chip bonding by at least one of a micro bump or a through silicon via (TSV) including a fine line width.

13. The computing device of claim 1, wherein the plurality of circuit chips and the interposer layer are connected to each other by at least one of a micro bump, a redistributed layer (RDL), or a through silicon via (TSV) including a fine line width.

14. The computing device of claim 1, wherein an electrode pad for the plurality of MEAs is disposed on the interposer layer or an upper portion of the substrate, and a bonding pad for the plurality of circuit chips is disposed on the upper portion of the substrate or a lower portion of the substrate.

15. The computing device of claim 1, wherein a total number of MEAs is same as a total number of circuit chips.

16. The computing device of claim 1, wherein the plurality of circuit chips and the plurality of MEAs are matched one-to-one or one-to-many.

17. The computing device of claim 1, wherein the interposer layer comprises a redistributed layer (RDL), and the plurality of circuit chips and the electrodes of the plurality of MEAs are connected to each other through the RDL.

18. The computing device of claim 1, wherein the substrate comprises one of a printed circuit board (PCB) and a silicon substrate.

19. The computing device of claim 1, wherein the plurality of MEAs are packaged to be waterproof.

20. The computing device of claim 1, further comprising:

a cell culture vessel comprising a cell culture medium that cultures the cells, wherein the electrode layer and the cell culture vessel are disposed adjacent to each other.

* * * * *